United States Patent [19]

Finizio

[11] 4,305,954

[45] Dec. 15, 1981

[54] ANTIINFLAMMATORY 3,4-DIHYDRO(OR 1,4-DIHYDRO)-2-[(SUBSTITUTED)THIO]-[1]BENZOPYRANO[3,4-d]IMIDAZOLES AND THEIR CORRESPONDING SULFOXIDES AND SULFONES

[75] Inventor: Michael Finizio, Wilmington, Del.

[73] Assignee: E. I. Du Pont de Nemours and Company, Wilmington, Del.

[21] Appl. No.: 233,653

[22] Filed: Feb. 11, 1981

[51] Int. Cl.³ ............... C07D 491/052; A61K 31/415
[52] U.S. Cl. .................................. 424/273 R; 548/323
[58] Field of Search ..................... 548/323; 424/273 R

[56] References Cited

U.S. PATENT DOCUMENTS 4,198,421  4/1980  Cherkofsky et al. ............... 548/323

OTHER PUBLICATIONS

D. Huckle et al., J. Med. Chem. 12(3), 277-279.
Dubroeucq, Chem. Abst. vol. 88, 1978, 88:136554h.

Primary Examiner—Henry R. Jiles
Assistant Examiner—Jane T. Fan

[57] ABSTRACT 3,4-Dihydro(or 1,4-dihydro)-2-[(substituted)thio]-[1]benzopyrano[3,4-d]imidazoles and their corresponding sulfoxides and sulfones, such as 7,8-dichloro-3,4-dihydro(or 1,4-dihydro)-2-[(1,1,2,2-tetrafluoroethyl)sulfonyl]-[1]benzopyrano[3,4-d]imidazole, are useful in the treatment of inflammation.

11 Claims, No Drawings

ANTIINFLAMMATORY 3,4-DIHYDRO(OR 1,4-DIHYDRO)-2-[(SUBSTITUTED)THIO]-[1]BENZOPYRANO[3,4-d]IMIDAZOLES AND THEIR CORRESPONDING SULFOXIDES AND SULFONES

FIELD OF INVENTION

This invention relates to benzopyranoimidazoles, their preparation, pharmaceutical compositions containing them and methods of using them to treat inflammation in mammals. More particularly, this invention relates to antiinflammatory 3,4-dihydro (or 1,4-dihydro)-2-[(substituted)thio]-[1]benzopyrano[3,4-d]imidazoles and their corresponding sulfoxides and sulfones.

PRIOR ART

D. Huckle et al., *J. Med. Chem.*, 12(3), 277-79 (1969) describe the synthesis of a compound of the formula:

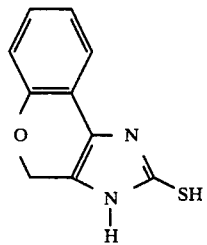

However, no biological activity is reported for this compound or compounds of related structure.

U.S. Pat. No. 4,198,421, issued Apr. 15, 1980, to Saul C. Cherkofsky and Thomas R. Sharpe, describes antiinflammatory 2-substituted-dibenzo[2,3:6,7]oxepino[4,5-d]imidazoles of the formula:

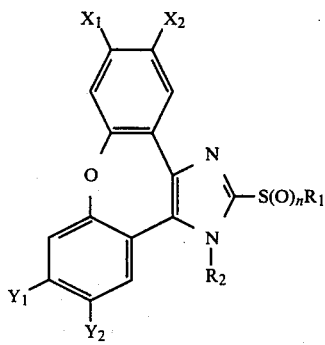

where
n is 0, 1 or 2;
$R_1$ is $CF_3$ or $CF_2CF_2H$;
$R_2$ is a variety of groups;
$X_1$ and $Y_1$ are independently H, Cl, F, dimethylamino or $C_1$-$C_2$ alkoxy; and
$X_2$ and $Y_2$ are independently H, F or Cl; provided at least one of $X_1$, $X_2$, $Y_1$ or $Y_2$ is other than H.

There is a continuing need for safe and effective antiinflammatory agents. Inflammation is a disease process characterized by redness, fever, swelling, and pain. Arthritis, in its various forms, is the most prevalent, chronic and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous sytem. Adrenocortical steroids produce gastric irritation and suppression of normal adrenal function.

The present invention results from efforts to develop new anti-arthritic compounds with good antiinflammatory activity and minimal side effects that could be more effective in treating arthritis than presently available drugs.

In addition to antiinflammatory properties, some compounds of this invention have demonstrated analgesic activity in a test procedure. This additional property is desirable in treatment of arthritis or related diseases; however, such compounds can be employed solely to alleviate pain.

SUMMARY OF THE INVENTION

According to the invention, there is provided a compound of the formula:

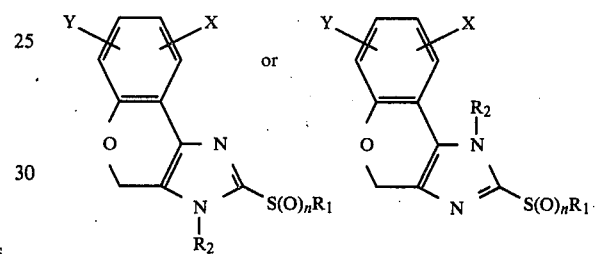

(Ia)      (Ib)

wherein
n is 0, 1 or 2;
$R_1$ is alkyl of 1 or 2 carbon atoms, or mono- or polyfluoroalkyl of 1 or 2 carbon atoms;
$R_2$ is H,

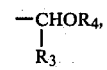

2-tetrahydropyranyl, 2-tetrahydrofuranyl, 4-nitrobenzyl, —$COOR_5$, —$COR_5$, —COAr or —$SO_2Ar$
where
$R_3$ is H or methyl;
$R_4$ is alkyl of 1-3 carbon atoms, benzyl, —$CH_2CH_2OCH_3$ or —$COR_5$;
$R_5$ is alkyl of 1-4 carbon atoms, or benzyl;
Ar is

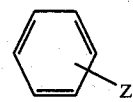

where Z is H, F, Cl, Br, alkyl of 1-4 carbon atoms, alkoxy of 1-4 carbon atoms or nitro;
with the proviso that when $R_2$ is 4-nitrobenzyl, n is 2 and when $R_2$ is —$COOR_5$, —$COR_5$, —COAr or —$SO_2Ar$, n is 0;
X and Y are independently H, F, Cl, Br, $NO_2$, alkoxy of 1 or 2 carbon atoms, —$N(C_{1-2}$ alkyl$)_2$, alkyl of 1 or 2 carbon atoms, —S(O)$_m$C$_{1-2}$ alkyl where m is 0, 1 or 2, provided at least one of X and Y is other than H; or a pharmaceutically suitable acid addition salt thereof when n is 0 or when X or Y is —N(C$_{1-2}$ alkyl)$_2$; or a pharmaceutically suitable metal salt thereof when n is 1 or 2 and R$_2$=H.

When R$_2$=H structures of the type Ia and Ib are tautomers.

There is also provided a process for preparing the aforesaid compounds which comprises:

(a) contacting a compound of the formula:

wherein X and Y are as defined above, with an alkylating agent suitable to introduce an R$_1$ group, and (b) optionally contacting the resulting compound with an oxidizing agent; and (c) optionally contacting a compound from step (a) or step (b) with an alkylating, acylating or sulfonylating agent suitable to introduce an R$_2$ group other than H.

Also provided are pharmaceutical compositions containing at least one of the aforesaid compounds and methods of using them to treat inflammation in mammals.

PREFERRED SCOPE

Compounds of preferred scope are those of Formula Ia or Ib or their salts where independently:
(1) n is 0 or 2; or
(2) R$_1$ is —CF$_3$ or —CF$_2$CF$_2$H; or
(3) X and Y are independently H, F, Cl, —OCH$_3$ or —NO$_2$ provided at least one is other than H; or
(4) R$_2$ is H.

Most preferred are compounds having the formula:

(IIa)          (IIb)

wherein
n is 0 or 2;
R$_1$ is —CF$_3$ or —CF$_2$CF$_2$H; and
X and Y are independently H, Cl, F, OCH$_3$ or NO$_2$, provided at least one is other than H.

Specifically preferred are compounds of Formula IIa or IIb where:
n is 0 or 2;
R$_1$ is —CF$_2$CF$_2$H; and
X and Y are H, F or Cl, provided at least one is other than H.

Preferably both X and Y are Cl.

PHARMACEUTICAL SALTS

Pharmaceutically suitable salts and their preparation are well known to those skilled in pharmaceuticals and any can be used in the present invention. Suitable salts of compounds where n is 0 or when X or Y is —N(C$_{1-2}$ alkyl)$_2$ include pharmaceutically suitable acid addition salts, preferably formed from mineral acids, and include hydrochloride, nitrate and sulfate. The acid used preferably has a pK$_a$ or not greater than 2.5.

Pharmaceutically suitable salts of compounds where n is 1 or 2 and R$_2$ is H include alkali metals and alkaline earth metals such as sodium, potassium and calcium.

SYNTHESIS

The compounds of this invention can be prepared from 3,4-dihydro(or 1,4-dihydro)-[1]benzopyrano[3,4-d]imidazole-2-thiols. The synthesis of the latter compounds involves conversion of the properly substituted ketones to the corresponding tosyloximes; these in turn are subjected to Neber rearrangement [P. W. Neber and A. Friedolsheim, *Ann.*, 449, 109 (1926)] and produce 3-amino-4-chromanone hydrochlorides which, upon treatment with potassium thiocyanate, give 3,4-dihydro(or 1,4-dihydro)-[1]benzopyrano[3,4-d]imidazole-2-thiols (Scheme I).

Scheme I

Preparation of the starting ketones can be accomplished by cyclization of the corresponding β-aryloxypropionic acids with phosphorous pentoxide, aluminum chloride, or sulfuric acid [P. F. Wiley, *J. Am. Chem. Soc.*, 73, 4205-9 (1951)], or hydrofluoric acid (Scheme II).

Scheme II

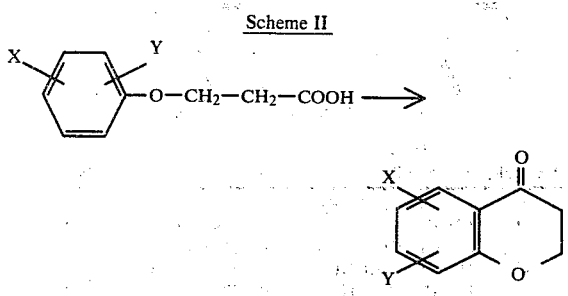

The sequence illustrated in Scheme I is reported by D. Huckle, I. M. Lockhart and M. Wright, *J. Med. Chem.*, 12(3), 277-79 (1969).

The 3-amino-4-chromanones of Scheme I can also be prepared by conversion of the ketones into isonitroso ketones (*Org. Syn.*, II, 363) and catalytic reduction of the latter [S. Kimoto et al., *Yakugaku Zasshi*, 88 (10), 1323-8, (1968)], (Scheme III).

Scheme III

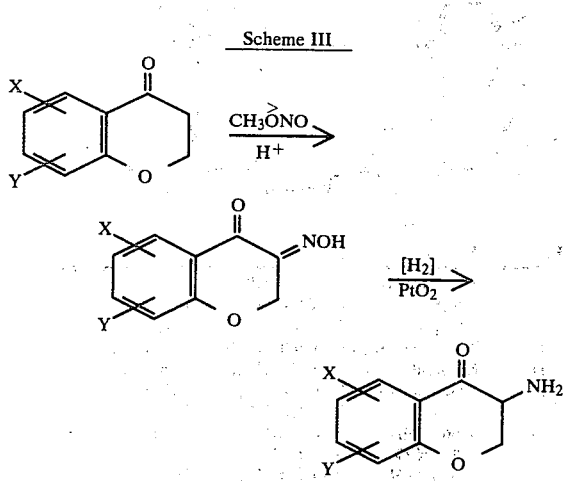

The appropriate $R_1$ group can be introduced by alkylating the 3,4-dihydro(or 1,4-dihydro)-[1]benzopyrano[3,4-d]imidazole-2-thiols with a suitable alkylating agent such as ethyl iodide or 2,2,2-trifluoroethyl trichloromethanesulfonate. Also, the 3,4-dihydro(or 1,4-dihydro)-[1]benzopyrano[3,4-d]imidazole-2-thiols can be reacted with tetrafluoroethylene to provide 2-[(1,1,2,2-tetrafluoroethyl)thio] derivatives. Similar addition reactions of tetrafluoroethylene and other fluorinated olefins are described in England, D. C, et al., *J. Am. Chem. Soc.*, 82, 5116 (1960) and Rapp, K. E., et al., *J. Am. Chem. Soc.*, 72, 3642 (1950). For the purpose of this disclosure tetrafluoroethylene and other fluorinated olefins used are considered alkylating agents.

Compounds where $R_1 = CF_3$ are preferably prepared by irradiating a mixture of the thiol and trifluoromethyl iodide as alkylating agent in liquid ammonia. An inert solvent such as ether, tetrahydrofuran or the like is usually added in order to have a homogeneous solution.

The 3,4-dihydro(or 1,4-dihydro)-2-[(substituted)thio]-[1]benzopyrano[3,4-d]imidazoles can then be oxidized to the corresponding sulfoxides or sulfones by using oxidizing agents such as m-chloroperbenzoic acid, [Tweit, R. C., et al., *J. Med. Chem.*, 16, 1161 (1973)]; sodium metaperiodate, [Leonard, N. J. and Johnson, C. R., *J. Org. Chem.*, 27, 282 (1962)]; hydrogen peroxide, [Kochergin, P. M. and Shchukina, M. N., *J. Gen. Chem. U.S.S.R.*, 25, 2289 (1955)], or potassium permangate, Rapp, K. E., et al., loc. cit.

Compounds of Formula Ia or Ib of this invention with $R_2$ other than H can be prepared by alkylation, acylation or sulfonylation of the corresponding compounds with n=0, 1 or 2 and $R_2=H$. These reactions can be conducted in the presence or absence of a base, such as potassium carbonate, pyridine, triethylamine, potassium t-butoxide, sodium hydride and the like. Examples of alkylating, acylating and sulfonylating agents capable of introducing other $R_2$ groups are 2-chlorotetrahydrofuran, 4-nitrobenzyl chloride, acetic anhydride, acetyl chloride, ethyl chloroformate, benzoyl chloride and benzenesulfonyl chloride and the like. Generally, a halide of an appropriate $R_2$ group, preferably a chloride, is used to introduce the $R_2$ group other than hydrogen. In the following examples, temperatures are in degrees centigrade.

PREPARATION OF INTERMEDIATES 6,7-Dichloro-2,3-dihydro-4-(hydroxyimino)-4H-1-benzopyran A mixture of 6,7-dichloro-2,3-dihydro-4H-1-benzopyran-4-one (59.7 g), methanol (750 ml), water (75 ml), potassium carbonate (76 g), hydroxylamine HCl (76.4 g) was heated at reflux for 4 hours, then poured into ice-water: the oxime of 6,7-dichloro-2,3-dihydro-4H-1-benzopyran-4-one was filtered off, washed with water, with a small volume of ether, then dried in air. Yield: 62.7 g; m.p. 192°-193°.

6,7-Dichloro-2,3-dihydro-4-[(4-methylphenyl)sulfonyloximino]-4H-1-benzopyran

A solution of p-toluenesulfonyl chloride (103 g) in 125 ml pyridine was added dropwise at 5°-10° to 6,7-dichloro-2,3-dihydro-4-(hydroxyimino)-4H-1-benzopyran (62.5 g) in 250 ml pyridine. The reaction mixture was then stirred for 20 hours at room temperature, poured into ice-water to separate out the title compound, which was filtered, washed several times with water, then once with ether, and finally dried in air. Yield: 101.8 g; m.p. 180°-184°.

3-Amino-6,7-dichloro-2,3-dihydro-4H-1-benzopyran-4-one Hydrochloride

A solution of sodium ethoxide in ethanol (from 6.5 g of sodium and 350 ml of ethanol) was added dropwise at 0°-5° to 6,7-dichloro-2,3-dihydro-4-(tosyloxyimino)-4H-1-benzopyran (100.5 g) in 1 liter of toluene. The reaction mixture was stirred at room temperature under nitrogen for 24 hours, filtered through Celite, washed with water, extracted with 1 N HCl. The combined acidic extracts were roto-evaporated and the residue was triturated with acetone to give the title compound in a crystalline form. Note: some product separated out during the extraction with aqueous HCl.

7,8-Dichloro-3,4-dihydro(or 1,4-dihydro)-[1]benzopyrano[3,4-d]imidazole-2-thiol

A mixture of 3-amino-6,7-dichloro-2,3-dihydro-4H-1-benzopyran-4-one HCl (10.2 g), acetic acid (80 ml), potassium thiocyanate (4.3 g) was heated at reflux for 20 minutes. After cooling, a solid product was filtered off and washed with water to give the title compound. Yield 8 g, m.p. >300°.

EXAMPLE 1

7,8-Dichloro-3,4-dihydro(or 1,4-dihydro)-2-[(1,1,2,2-tetrafluoroethyl)-thio]-[1]benzopyrano[3,4-d]imidazole To a stainless steel tube was added 7,8-dichloro-3,4-dihydro(or 1,4-dihydro)-[1]benzopyrano[3,4-d]imidazole-2-thiol (11.4 g, 0.042 mole), dimethylformamide (240 ml) and diisopropylamine (4.2 g). Subsequent to purging the tube several times with dry nitrogen, tetrafluoroethylene (4.2 g, 0.042 mole) was introduced. The tube was agitated at 50° for 8 hours. The reaction mixture was poured into water and extracted with ethyl acetate. The organic phase was dried over magnesium sulfate and roto-evaporated. The residue was triturated with hot toluene to give the title compound, m.p. 210°–212° (dec.).

EXAMPLE 2

7,8-Dichloro-3,4-dihydro(or 1,4-dihydro)-2-[(1,1,2,2-tetrafluoroethyl)sulfonyl]-[1]benzopyrano[3,4-d]imidazole To a solution of 7,8-dichloro-3,4-dihydro(or 1,4-dihydro)-2-[(1,1,2,2-tetrafluoroethyl)thio]-[1]benzopyrano[3,4-d]imidazole (3.2 g, 0.01 mole) in ethyl acetate (30 ml) was added portionwise 86.4% m-chloroperbenzoic acid (4.5 g, 0.023 mole). The mixture was stirred at room temperature for 1 hour, then washed with 10% sodium bicarbonate. The organic phase was dried with magnesium sulfate and stripped of solvent. The resulting product was purified by chromatography using a silica gel column and toluene-ethyl acetate (1:2) as eluent. Yield: 2.2 g; m.p. 218°–219° (dec.).

EXAMPLE 3

7,8-Dichloro-3,4-dihydro (or 1,4-dihydro)-2-[(trifluoromethyl)-thio][1]benzopyrano[3,4-d]imidazole Liquid ammonia (125 ml) was condensed in a flask containing 7,8-dichloro-3,4-dihydro(or 1,4-dihydro)-[1]benzopyrano[3,4-d]imidazole-2-thiol (4 g, 0.015 mole) and tetrahydrofuran (50 ml) was added to obtain a homogeneous solution. This mixture was cooled to −78° and treated with trifluoromethyl iodide (2.5 ml) added slowly as a gas. When the addition was completed the cooling bath was removed and the reaction mixture was irradiated for 4 hours with a General Electric 275 w sun lamp. The ammonia was then allowed to evaporate, the solvent was stripped on a roto-evaporator and the resulting residue washed with water and recrystallized from toluene to give the title compound, m.p. 212°–216° (dec.).

Other 3,4-dihydro(or 1,4-dihydro)-2-[(substituted)thio]-[1]benzopyrano[3,4-d]imidazoles and their corresponding sulfones that were prepared by the procedures described in Examples 1, 2 and 3 are given in Table I.

TABLE I

| Example | X | Y | $R_1$ | n | m.p.(°C.) | Yield (%) |
|---|---|---|---|---|---|---|
| 1 | Cl | Cl | $CF_2CHF_2$ | 0 | 210–212° | 62 |
| 2 | Cl | Cl | $CF_2CHF_2$ | 2 | 218–219° | 58 |
| 3 | Cl | Cl | $CF_3$ | 0 | 212–216° | 37 |
| 4 | H | Cl | $CF_2CHF_2$ | 0 | 192.5–193.5° | 36 |
| 5 | F | H | $CF_2CHF_2$ | 0 | 170–173° | 42 |
| 6 | F | H | $CF_2CHF_2$ | 2 | 151–153° | 20 |

Following the procedures described, the following 3,4-dihydro(or 1,4-dihydro)-2-[(substituted)thio]-[1]benzopyrano[3,4-d]imidazoles and their corresponding sulfoxides and sulfones can be prepared.

TABLE II

| Example | X, Y | n | $R_1$ | $R_2$ |
|---|---|---|---|---|
| 7 | 7,8-dichloro | 1 | $CF_2CHF_2$ | H |
| 8 | 7-$NO_2$ | 0 | $CF_2CHF_2$ | H |
| 9 | 7-$SCH_3$ | 0 | $CF_3$ | H |
| 10 | 7,8-dimethoxy | 0 | $CF_2CHF_2$ | 2-tetrahydrofuranyl |
| 11 | 6,9-dichloro | 0 | $CF_2CHF_2$ | $COOC_2H_5$ |
| 12 | 6,8-dichloro | 0 | $CF_2CHF_2$ | $CO-CH_3$ |
| 13 | 6-Br | 2 | $CF_2CHF_2$ | H |
| 14 | 6,7-dichloro | 0 | $CHF_2$ | 2-tetrahydropyranyl |
| 15 | 7-$N(CH_3)_2$ | 0 | $CH_3$ | H |
| 16 | 7-$N(C_2H_5)_2$ | 0 | $CF_2CHF_2$ | H |
| 17 | 7-$OC_2H_5$ | 2 | $CF_2CHF_2$ | H |
| 18 | 6-Cl, 9-$CH_3$ | 0 | $CF_3$ | H |
| 19 | 7-$CH_3$ | 2 | $C_2H_5$ | H |
| 20 | 7,8-dichloro | 2 | $CF_2CHF_2$ | 4-$NO_2C_6H_4CH_2-$ |
| 21 | 7-$SO_2CH_3$ | 0 | $CF_2CHF_2$ | $SO_2C_6H_5-$ |
| 22 | 7,8-dichloro | 0 | $CF_2CHF_2$ | $-COC_6H_5$ |
| 23 | 7,8-dichloro | 0 | $CH_2CF_3$ | H |
| 24 | 7,8-dichloro | 0 | $CF_2CH_2F$ | H |

DOSAGE FORMS

The antiinflammatory agents of this invention can be administered to treat inflammation by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl or propyl-paraben, and chlorobutanol.

Suitable pharmaceutical carriers are described in *Remington's Pharmaceutical Sciences*, E. W. Martin, a standard reference text in this field.

Useful pharmaceutical dosage forms for administration of the compounds of this invention can be illustrated as follows:

Capsules

A large number of unit capsules are prepared by filling standard two-piece hard gelatin capsules each with 75 milligrams of powdered active ingredient, 150 milligrams of lactose, 24 milligrams of talc, and 6 milligrams magnesium stearate.

Soft Gelatin Capsules

A mixture of active ingredient in soybean oil is prepared and injected by means of a positive displacement pump into gelatin to form soft gelatin capsules containing 75 milligrams of the active ingredient. The capsules are washed in petroleum ether and dried.

Tablets

A large number of tablets are prepared by conventional procedures so that the dosage unit is 75 milligrams of active ingredient, 6 milligrams of magnesium stearate, 70 milligrams of microcrystalline cellulose, 11 milligrams of cornstarch and 200 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by commonly used techniques.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Injectable

A parenteral composition suitable for administration by injection is prepared by dissolving 1% by weight of active ingredient in sodium chloride injection U.S.P. XX and adjusting the pH of the solution to between 6 and 7. The solution is sterilized by commonly used techniques.

USE

To detect and compare the antiinflammatory activities of compounds in this series and standard drugs, a test was used based on a standard model of arthritis for which there is good correlation with human efficacy. The model is adjuvant-induced arthritis in rats. *Federation Proceedings*, Vol. 32, No. 2, 1973 "Models Used for the Study and Therapy of Rheumatoid Arthritis'-'—Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

ESTABLISHED ADJUVANT-INDUCED ARTHRITIS IN RATS

Charles River Lewis male rats (130-150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant-injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\text{Arthritic Control} - \text{Treatment Group}}{\text{Arthritic Control} - \text{Non-Arthritic Control}} \times 100 =$$
$$\text{Mean Paw Volume (ml)} - \text{Mean Paw Volume (ml)}$$

% Decrease from Control Mean Paw Volume.

Dose-response regression lines of the percent decrease are plotted on semi-log paper by visual fit and the ED50% decrease from control paw volume is determined by inspection. Data for some of the compounds in this invention are summarized in Table III.

Compounds from this series were also compared to indomethacin, phenylbutazone, ibuprofen, and aspirin.

TABLE III
Antiarthritic Activity

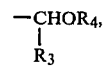

| Example | X | Y | $R_2$ | $R_1$ | n | Adjuvant Arthritis $ED_{50}$(mg/kg) |
|---|---|---|---|---|---|---|
| 1 | Cl | Cl | H | $CF_2CHF_2$ | 0 | 8.2 |
| 2 | Cl | Cl | H | $CF_2CHF_2$ | 2 | 3.1 |
| 4 | H | Cl | H | $CF_2CHF_2$ | 0 | >9(30%)* |
| 5 | F | H | H | $CF_2CHF_2$ | 0 | 50 |
| 6 | F | H | H | $CF_2CHF_2$ | 2 | >9(22%)* |
| Indomethacin | | | | | | 0.3 |
| Phenylbutazone | | | | | | 10 |
| Ibuprofen | | | | | | 100 |
| Aspirin | | | | | | 305 |

*values in parenthesis indicates % reduction at the indicated dose.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

What is claimed is:

1. A compound of the formula:

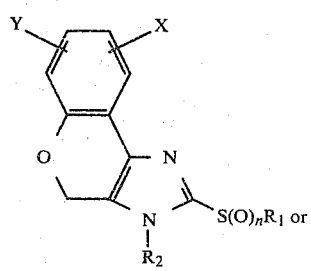

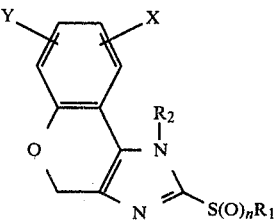

wherein
n is 0, 1 or 2;
$R_1$ is alkyl of 1 or 2 carbon atoms, or mono- or polyfluoroalkyl of 1 or 2 carbon atoms;
$R_2$ is H, $$-\underset{R_3}{\overset{|}{C}}HOR_4,$$

2-tetrahydropyranyl, 2-tetrahydrofuranyl, 4-nitrobenzyl, —$COOR_5$, —$COR_5$, —$COAr$ or —$SO_2Ar$ where
$R_3$ is H or methyl;
$R_4$ is alkyl of 1–3 carbon atoms, benzyl, —$CH_2CH_2OCH_3$ or —$COR_5$;
$R_5$ is alkyl of 1–4 carbon atoms, or benzyl;
Ar is

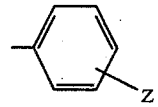

where Z is H, F, Cl, Br, alkyl of 1–4 carbon atoms, alkoxy of 1–4 carbon atoms or nitro;
with the proviso that when $R_2$ is 4-nitrobenzyl, n is 2 and when $R_2$ is —$COOR_5$, —$COR_5$, —$COAr$ or —$SO_2Ar$, n is 0;
X and Y are independently H, F, Cl, Br, $NO_2$, alkoxy of 1 or 2 carbon atoms, —$N(C_{1-2}$ alkyl$)_2$, alkyl of 1 or 2 carbon atoms, —$S(O)_mC_{1-2}$ alkyl where m is 0, 1 or 2, provided at least one of X and Y is other than H; or
a pharmaceutically suitable acid addition salt thereof when n is 0 or when X or Y is —$N(C_{1-2}$ alkyl$)_2$; or
a pharmaceutically suitable metal salt thereof when n is 1 or 2 and $R_2$=H.

2. A compound of claim 1 wherein n is 0 or 2.

3. A compound of claim 1 wherein $R_1$ is $CF_3$ or $CF_2CF_2H$.

4. A compound of claim 1 wherein X and Y are independently H, F, Cl, —$OCH_3$ or —$NO_2$ provided at least one is other than H.

5. A compound of claim 1 wherein $R_2$ is H.

6. A compound of the formula:

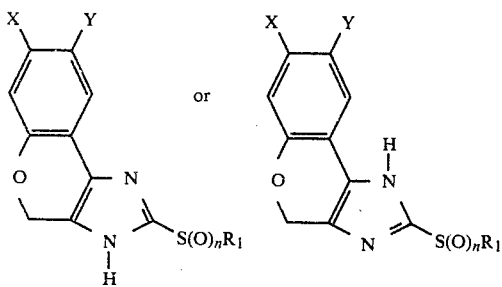

wherein n is 0 or 2;

$R_1$ is —$CF_3$ or —$CF_2CF_2H$; and

X and Y are independently H, Cl, F, $OCH_3$ or $NO_2$, provided at least one is other than H.

7. A compound of the formula:

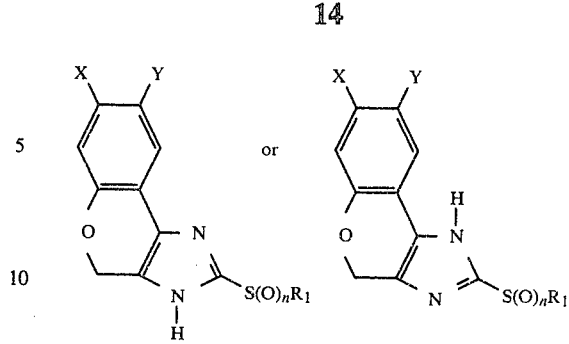

wherein
n is 0 or 2;
$R_1$ is —$CF_2CF_2H$; and
X and Y are independently H, F, or Cl, provided at least one is other than H.

8. A compound of claim 7 wherein both X and Y are Cl.

9. The compound of claim 8 which is 7,8-dichloro-3,4-dihydro(or 1,4-dihydro)-2-[(1,1,2,2-tetrafluoroethyl)sulfonyl]-[1]benzopyrano[3,4-d]imidazole.

10. A pharmaceutical composition consisting essentially of a suitable pharmaceutical carrier and an effective antiinflammatory amount of a compound of claim 1 or of claim 2 or of claim 3 or of claim 4 or of claim 5 or of claim 6 or of claim 7 or of claim 8 or of claim 9.

11. A method of treating inflammation in a mammal which comprises administering to the mammal an effective antiinflammatory amount of a compound of claim 1 or of claim 2 or of claim 3 or of claim 4 or of claim 5 or of claim 6 or of claim 7 or of claim 8 or of claim 9.

* * * * *